(12) United States Patent
Kirkham (10) Patent No.: US 8,343,182 B2
(45) Date of Patent: Jan. 1, 2013

(54) TOURNIQUET ASSEMBLY

(76) Inventor: Jeffrey B. Kirkham, Portland, OR (US)

( * ) Notice: Subject to any disclaimer, the term of this patent is extended or adjusted under 35 U.S.C. 154(b) by 621 days.

(21) Appl. No.: 12/553,831

(22) Filed: Sep. 3, 2009

(65) Prior Publication Data

US 2010/0057120 A1 Mar. 4, 2010

Related U.S. Application Data

(60) Provisional application No. 61/190,964, filed on Sep. 4, 2008, provisional application No. 61/197,084, filed on Oct. 23, 2008.

(51) Int. Cl.
*A61B 17/00* (2006.01)
*A61F 5/37* (2006.01)
(52) U.S. Cl. .................. 606/203; 606/201; 128/876
(58) Field of Classification Search .................. None
See application file for complete search history.

(56) References Cited

U.S. PATENT DOCUMENTS

| 6,149,618 | A * | 11/2000 | Sato | 602/75 |
| 6,427,697 | B1 * | 8/2002 | Pearcey | 128/876 |
| 6,682,547 | B2 * | 1/2004 | McEwen et al. | 606/202 |
| 6,899,720 | B1 * | 5/2005 | McMillan | 606/203 |
| 2005/0273134 | A1 * | 12/2005 | Esposito | 606/203 |
| 2006/0167492 | A1 * | 7/2006 | Prince | 606/203 |

OTHER PUBLICATIONS

Narragansett Leathers, U.S. Pub. Hoof Pick Belts, Jan. 31, 2002.*
Author Unknown, Combat Application Tourniquet, retrieved 2008, www.combattourniquet.com/index.php.

* cited by examiner

*Primary Examiner* — Katherine Dowe
*Assistant Examiner* — Sidharth Kapoor
(74) *Attorney, Agent, or Firm* — : Workman Nydegger (57) ABSTRACT

A tourniquet assembly includes a strap and a windlass crank attached to a windlass cord that forms a loop that is slidably engaged with anchors that are attached to the main strap. During use, the crank is rotated, causing the windlass cord to twist. This effectively shortens the length of the windlass cord which also pulls the anchors inwardly, thereby causing a similar shortening of the main strap between the anchors and enabling the strap to be used for use as a tourniquet.

23 Claims, 12 Drawing Sheets

TOURNIQUET ASSEMBLY

CROSS-REFERENCE TO RELATED APPLICATIONS

This application claims the benefit of U.S. Provisional Patent Application 61/190,964 filed Sep. 4, 2008, titled "INTEGRATED WINDLASS TOURNIQUETS", and U.S. Provisional Patent Application 61/197,084 filed Oct. 23, 2008, titled "WINDLASS PULLEY TOURNIQUET SLING". Both of the foregoing applications are incorporated by reference in their entirety.

BACKGROUND OF THE INVENTION

The Relevant Technology

Various types of tourniquets have been used when necessary to stop the flow of blood through an injured arm or leg so as to prevent death of the injured through loss of blood. However, tourniquets are typically carried as a separate piece of gear, adding additional weight and bulk to the already substantial gear that a soldier or emergency services person must carry on his or her person. Further, depending on how/when a tourniquet is carried, access to and/or efficient use of the tourniquet can be difficult. These difficulties can be compounded when an injured person attempts to fix the tourniquet on him or herself or another injured person. For example, even if the tourniquet is accessible, it may be very difficult to apply the tourniquet to one of the person's own arms with the use of only the remaining hand. Further, the environment within which the user finds himself during fixing of the tourniquet can be an issue (e.g., within a collapsing building or under enemy fire).

BRIEF SUMMARY OF THE PREFERRED EMBODIMENTS

The present invention is directed to windlass tourniquet assemblies that are integrated into belts, harnesses, straps, slings (such as rifle slings), or other similar objects. The present invention also includes methods for applying the integrated tourniquets and assemblies. For example, in one embodiment, a windlass tourniquet assembly includes an elongate main strap extending between a first end and an opposite second end, and attachment means (e.g., a buckle) for attaching the first end of the main strap to the second end of the strap. At least a portion of the attachment means is disposed at the first end of the elongate main strap. The assembly further includes a windlass strap extending between a first and second end, the first end of the windlass strap being secured to a front surface of the main strap at the first end of the main strap near the buckle or other attachment means. The second end of the windlass strap is secured to the main strap at a location a predetermined distance away from the attachment means.

Anchor means for anchoring the attachment means in a position for applying the tourniquet may be disposed on a back surface of the main strap opposite the main strap's front surface. One example of anchor means is an anchor strap including a plurality of loops formed by attaching (e.g., stitching) the anchor strap to the main strap at a plurality of locations along the length of the anchor strap. The assembly also includes an elongate windlass crank that is attachable to the windlass strap during use so that when the crank is rotated the windlass strap is twisted, effectively shortening the length of the windlass strap and thereby tightening the main strap (as a result of the attachment of the windlass strap to the main strap) for use as a tourniquet.

According to some embodiments, tourniquets also include pulley means for tightening the tourniquet and without requiring the main tourniquet strap to be twisted and in such a way as to minimize or reduce bunching of the main tourniquet strap. The pulley means also provides a mechanical advantage when rotating the windlass for tightening the tourniquet, as described herein.

Other embodiments include an elongate main strap extending between a first end and an opposite second end. Attachment means attach the first end of the main strap to the second end of the main strap. At least a portion of the attachment means is disposed at a first end of the elongate main strap. A windlass pulley cord extends between the first and second ends. A pulley anchor near the attachment means secures the first end to the main strap at the first end of the main strap. A second pulley anchor at a location a predetermined distance away from the attachment means secures the second end of the windlass pulley cord to the main strap. An elongate windlass crank is also attached to the windlass pulley cord during use so that when the crank is rotated, the windlass pulley cord is twisted, effectively shortening the length of the windlass pulley cord and thereby tightening the main strap for use as a tourniquet.

These and other objects and features of the present invention will become more fully apparent from the following description, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention includes various articles of manufacture, such as, but not limited to belts, slings, harnesses and other objects incorporating windlass tourniquet assemblies and components and/or pulley assemblies and components that can be used in the application of a tourniquet.

According to some embodiments, the windlass tourniquet components are specifically configured to facilitate use and application in a quick and efficient manner, particularly in limited light conditions, in self-application conditions and even when the person applying the tourniquet has use of only a single hand. Improved accessibility, any reduction in weight and/or the sheer number of objects that must be carried by the user, while retaining essentially the same capability would be a welcome improvement.

According to one embodiment, a windlass tourniquet is integrated into a belt comprising an elongate strap and a buckle as well as other additional windlass tourniquet components. The windlass tourniquet configuration of the present invention can be integrated into military style belts composed of Nylon webbing straps and double pass buckles, although other types of belts, materials and buckles can also be configured for use with the windlass tourniquet components of the present invention.

The windlass tourniquet configurations of the present invention can also be integrated into rifle slings, harnesses and other types of objects having straps and buckles. Accordingly, while the attached Figures show some belt configurations, it will be appreciated that the elongate straps and buckles of the belts shown in the Figures can also comprise straps and buckles of a harness or rifle sling, as well as other objects such that embodiments of the invention also include slings, straps and harnesses having integrated windlass tourniquets. It will be appreciated that when tourniquets are incorporated into slings and harnesses, such inventive slings and harnesses can include any additional features (e.g., attachment means such as buckles, hooks, and so forth) used for attaching the slings and harnesses to the guns, bags, or other corresponding objects.

II. Windlass Tourniquet Embodiments

Figure 1A:
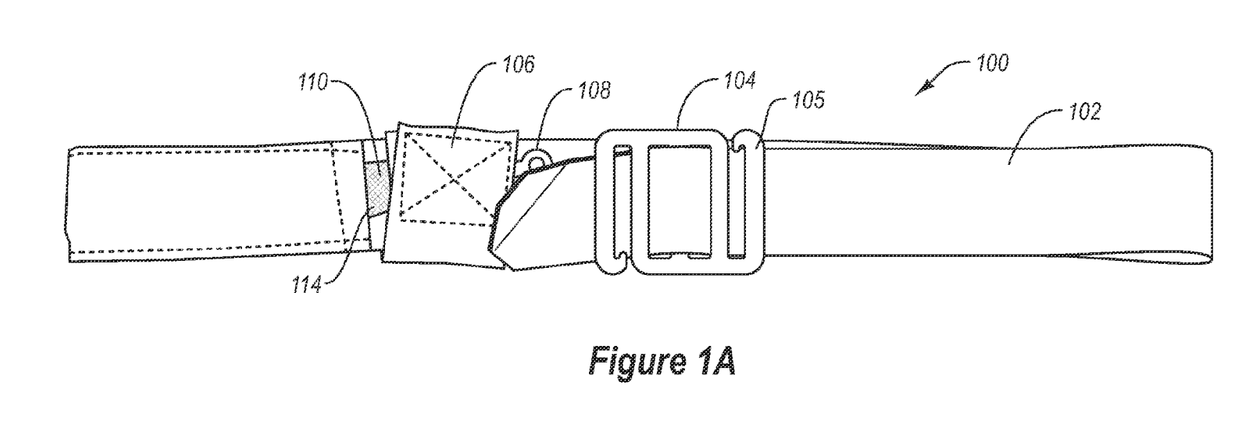
FIGS. 1A-1B show perspective views of exemplary windlass tourniquet assemblies shown in a fastened state, with the straps passing through the buckles.
Figure 1B:
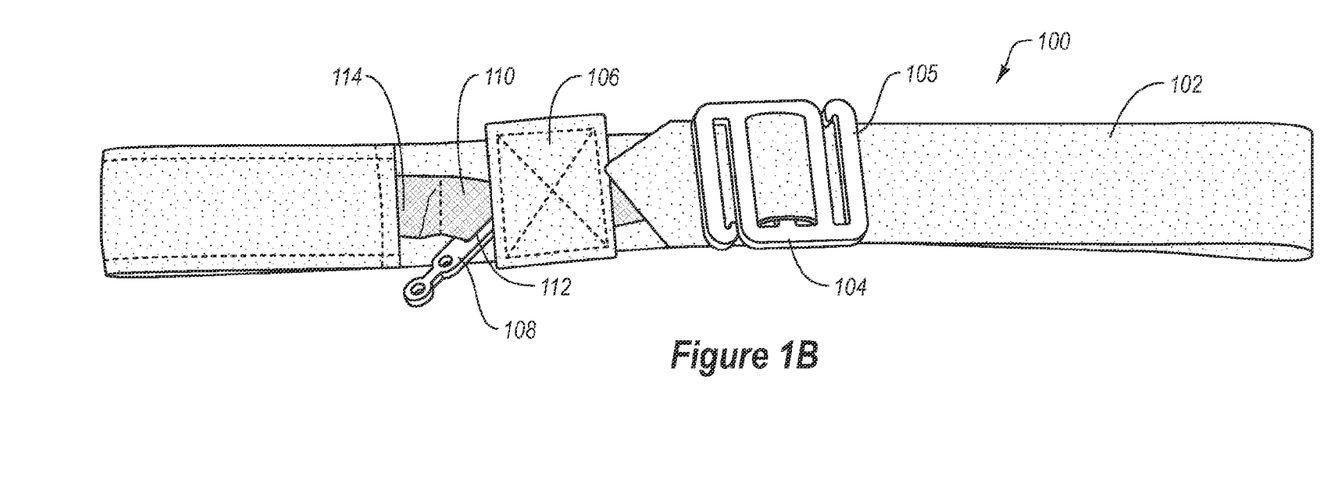

In FIGS. 1A-1B, two examples of windlass tourniquet belts 100 utilizing Nylon straps 102 and double pass buckles 104 are shown. Both of these belts 100 are essentially the same, except for the color and materials used. As shown, the double pass buckles 104 of the belts 100 are configured to receive and securely fasten the belt straps 102 in place when the straps 102 are passed through the buckles 104.

Figure 2A:
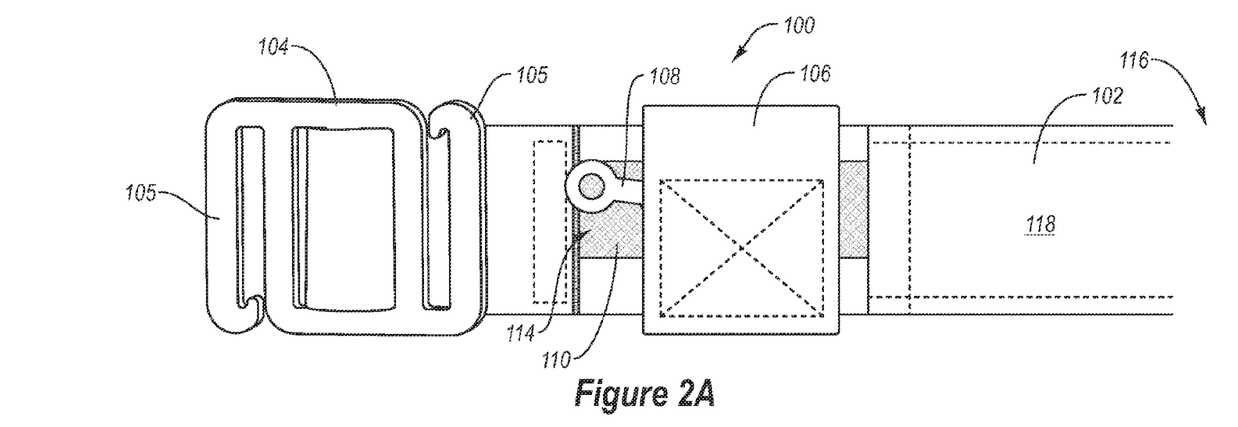
FIGS. 2A-2B show the first ends of each assembly of FIGS. 1A-1B, respectively, in an unfastened state.
Figure 2B:
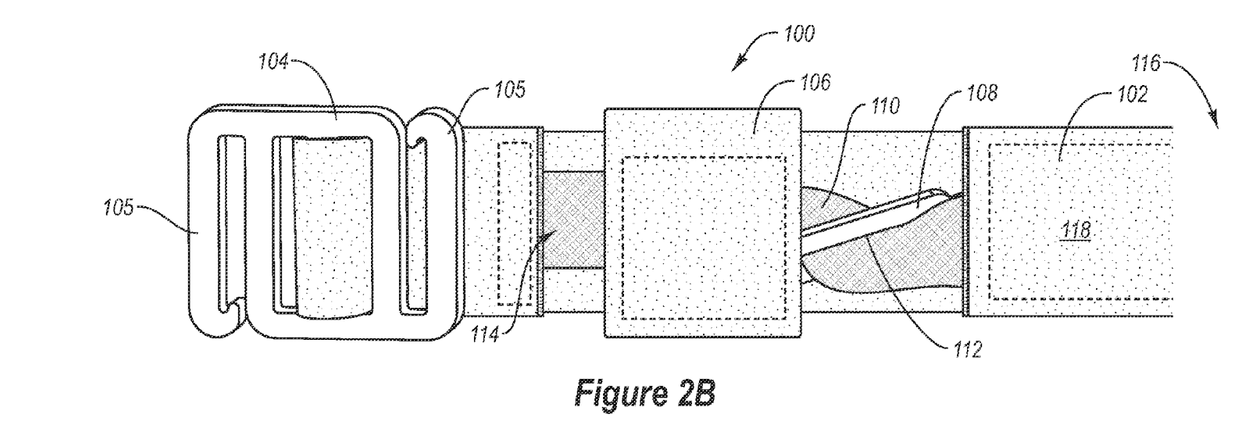

In FIG. 1, the belts 100 are shown in a fastened state, with the straps 102 passing through the buckles 104. In FIGS. 2A-2B, the belts 100 are shown in an unfastened state.

It will be appreciated that the width, thickness and length of the belts 100, as well as the material composition of the belts 100 can be altered to accommodate different needs and preference. According to one embodiment, the main strap 102 of the belt 100 is configured with a length of about 30-50 inches and more preferably a length of about 35-45 inches. The belt strap 102 also has a width in the range of 1-3 inches, and more preferably a width in the range of about 1.75 inches and 2.25 inches. The size and dimensions of the strap 102 can also be modified when the strap 102 is used as a harness strap or a rifle sling.

Some of the windlass tourniquet components corresponding to belt 100 are visible in FIGS. 1A through 2B, although in a secured state by additional Nylon strapping 106 that lays substantially perpendicular to the linear length of the main belt strap 102. This additional Nylon strapping 106 is one example of securing means for securing some of the other windlass tourniquet components in place, such as a windlass crank 108 which is unsecured and plainly visible in FIGS. 3A-3B.

Figures 3A, 3B:
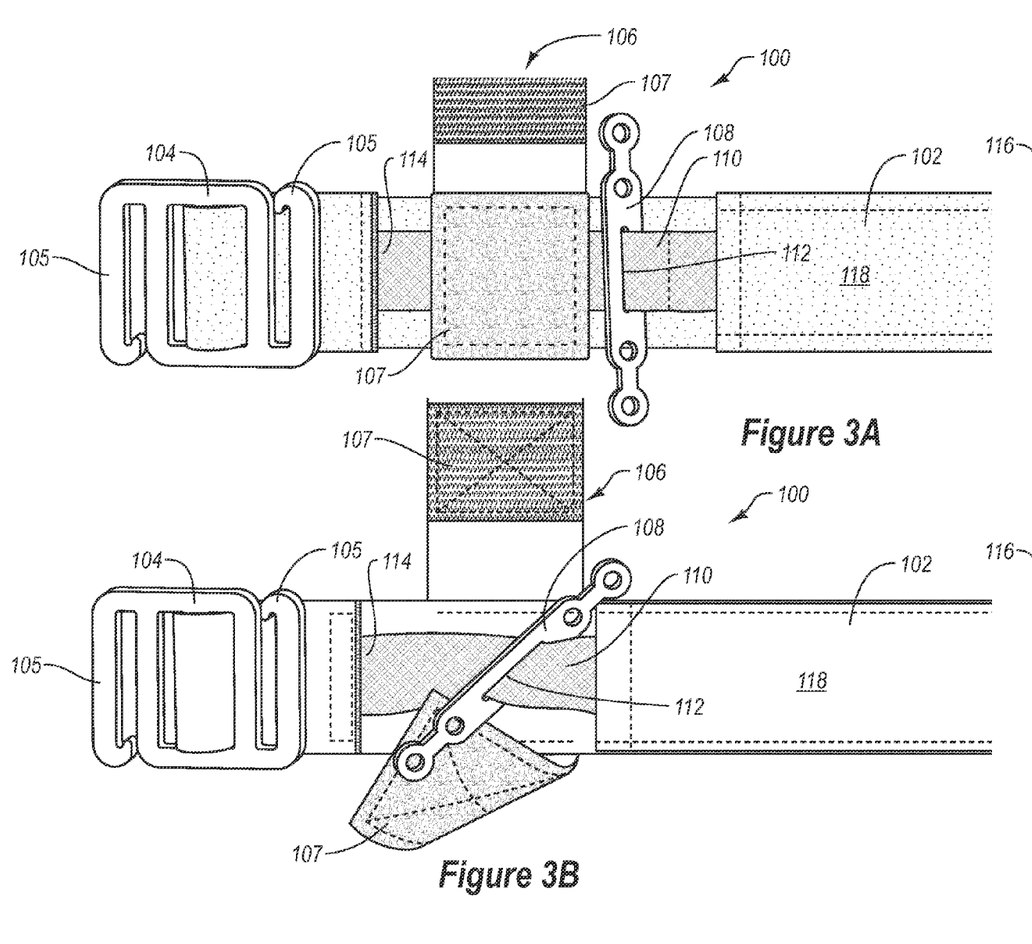
FIGS. 3A-3B show views similar to FIGS. 2A-2B respectively, and showing a windlass crank held in place by a windlass strap that passes through a hole disposed within the center of the windlass crank.

As shown in FIGS. 3A-3B, a windlass crank 108 is held in place by a windlass strap 110 that passes through a hole 112 disposed within the center of the windlass crank 108. The windlass strap 110 is also secured to the main strap 102 at a first end 114 of the belt 100, near the buckle 104, as well as at a second portion of the main strap 102 such as at the alternate end 116 of the belt 100, a middle section of the belt 100 or any other portion of the belt 100 a predetermined distance away from the buckle 104. The windlass strap 110 can be secured to the main strap 102 of belt 100 with stitching, adhesives, plastic welding, or any other attachment means.

According to one embodiment, the windlass strap 110 is only a few inches in length (e.g., two to four inches). In other embodiments, the windlass strap 110 extends between about 30 inches and 40 inches in length along the belt 100 (i.e., most of the length of the elongate strap 102) and is secured to the belt 100 by a sleeve material 118 that hides and protects most of the windlass strap 110. Although not necessary, the windlass strap 110 is shorter than the entire length of the belt so that the belt includes at least 6 inches to a foot of Nylon webbing 102 that does not include the windlass strap 110 and that is more easily passed through the buckle 104 (i.e., as a result of decreased thickness) than a portion of the main strap 102 of belt 100 that includes the windless strap 110.

FIGS. 3A-3B illustrate how the securing straps 106 are configured with Velcro® hook and loop material 107 on alternate sides, so that the securing straps 106 can be securely positioned around the windlass crank 108 and in such a manner as to hold the windlass crank 108 in a substantially secure position. It will be appreciated, however, that other means can also be included with the securing straps so as to releasably secure the straps in a desired placement, such as zippers, buttons, snaps, and so forth. FIGS. 2A-2B illustrate the securing straps 106 in a closed configuration, securing the windlass crank 108 in a substantially fixed position.

Figure 4:
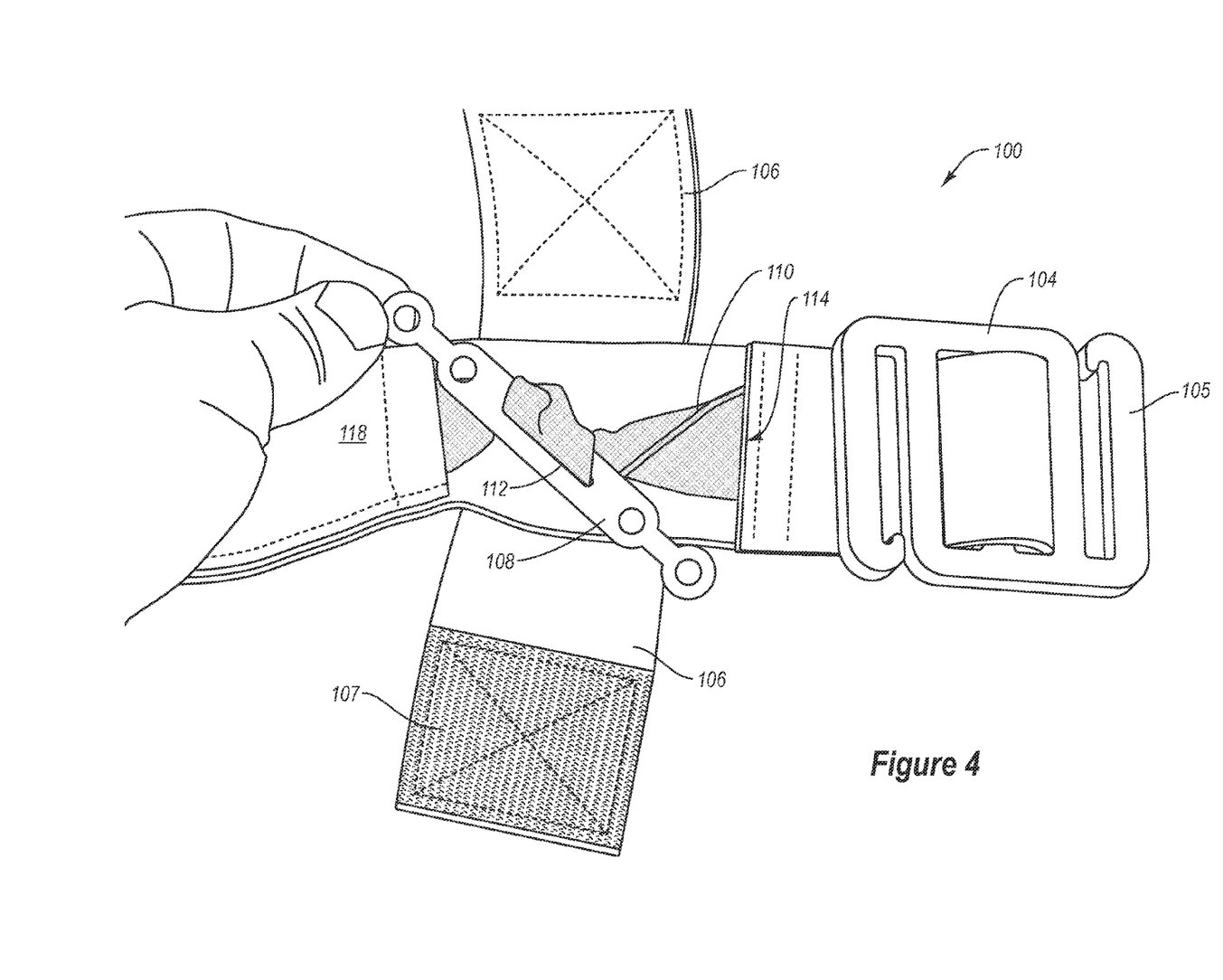
FIG. 4 shows how the windlass crank, when rotated, causes the windlass strap passing through the windlass crank to be twisted and pulled tight.

The windlass crank 108, when rotated, causes the windlass strap 110 passing through the windlass crank 108 to be twisted and pulled tight. One example of this is shown in FIG. 4. As shown, the windlass crank 108 has been rotated about 90° or about a quarter turn, by hand, and the windlass strap 110 has been twisted in such a way as to effectively shorten the length of the strap 110 and tightening the strap 110. Because the windlass strap 110 is attached to the main elongate strap 102 of belt 100 at two locations (i.e., 114 and 116), the tightening of the strap 110 also tightens or pulls the belt 100 together between the two locations that the strap 110 is attached to, thereby providing a force for tightening the main elongate strap 102 of belt 100 when the belt 100 is utilized as a tourniquet, as described in more detail below. In this manner, the windlass crank 108 and windlass strap 110 represent one example of a means for tightening the belt.

In some embodiments, the windlass crank 108 is configured in size and shape to be rotated or twisted by a single hand. The length of the windlass crank 108 in some embodiments is about 2-3 inches. In other embodiments, the length of the windlass crank 108 is more than 3 inches. The windlass crank 108 can be manufactured out of virtually any material that is sufficiently strong to provide the necessary structural integrity to remain straight (unbent) when the windlass crank 108 torque forces are applied during rotation of the windlass crank 108. In one embodiment, the crank 108 is manufactured out of steel. In another embodiment the crank 108 is manufactured out of a lighter material, such as aluminum. Although not necessary, the ends of the crank 108 can also be textured to facilitate gripping and rotation of the crank 108 by hand. The texturing can be provided by grooves formed in the crank 108, by a rubber material or another material disposed on the ends of the crank 108, or any other texturing means.

Figure 5A:
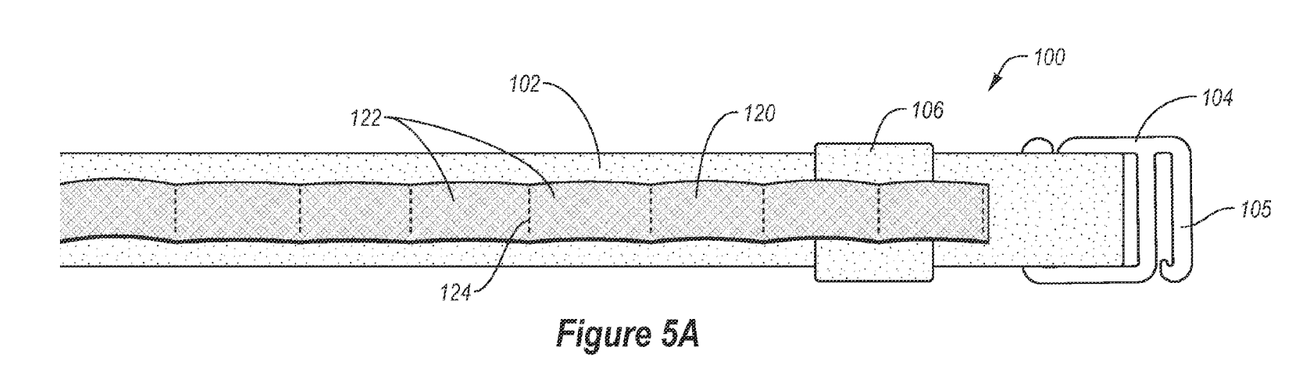
FIGS. 5A-5B show the back side of the elongate main strap, which in the illustrated embodiment is also the inside of the person's belt when the belt is worn as a belt, used as a harness, or used as a rifle sling. As shown, the belt includes an anchor strap attached to the back side of the belt.
Figure 5B:
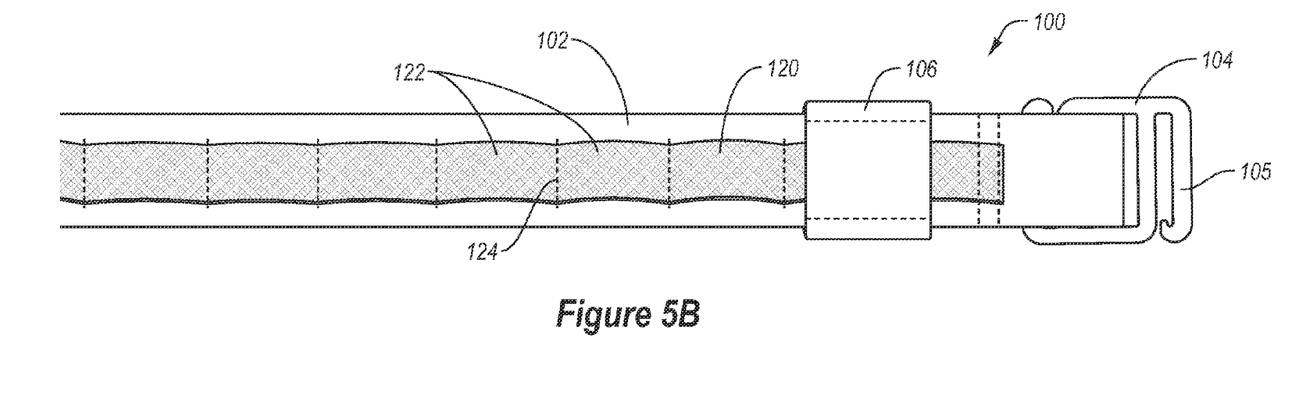

Attention is now directed to FIGS. 5A-5B, which shows the back side of the belt 100. The back side of the belt 100 is also the inside of the belt, when the belt 100 is worn as a belt, used as a harness, or used as a rifle sling. As shown, the belt 100 includes an anchor strap 120 attached to the belt. The anchor strap 120 is one example of an anchor means for anchoring the buckle 104 in a tourniquet position (e.g., a position for applying a tourniquet). Other examples of anchoring means include holes, hooks, and other objects configured to securely hold the buckle 104 of the belt 100 or an end of the belt 100 in a tourniquet ready position. The shape, size and quantity of the anchors that are positioned within the belt can vary to accommodate different needs and preferences. The location of the anchors can also vary to accommodate different tourniquet requirements, as described in more detail below.

In one embodiment, the anchor strap 120 includes a plurality of loops 122 that are formed by sewing or otherwise attaching the anchor strap 120 to the belt in different locations 124 and that extend substantially the entire length of the belt 100. The loops 122 can also be formed by attaching independent loops to the belt 100 (not shown). In the present embodiment, the loops 122 are about 2 inches in length. In other embodiments, the loops 122 are smaller or larger. While the loops 122 are shown to extend the full length of the anchor strap 120, it will be appreciated that in other embodiments (not shown), the anchor strap 120 only includes a few anchors that are placed along only a portion of the belt 100. According to one preferred embodiment, the loops 122 or other anchor placements extend about 20-35 inches along the back side of the elongate main strap 102 of belt 100, and even more preferably about 26-30 inches along the back of the belt 100.

Although the foregoing anchoring means comprising loops 122 have been described in detail, it will be appreciated that different types of anchoring means can also be used. For example, in one embodiment (not shown), the anchors are not loops 122, but are, instead, holes passing through the main Nylon webbing of the belt 100 and which are reinforced by grommets. Other types of anchors and anchoring means can also be used.

The anchors or loops 122 can also be made with the same or different materials that are used to form the main strap 102 of the belt 100. In one embodiment, the anchor strap 120 or other anchor means are formed from a different color than a color of the main belt 102. For example, the anchors or loops 122 might be white, yellow, red or another color that is different than the main strapping 102 of a black or green belt. This color contrast can help aid in the detection of the loops 122 and to facilitate the placement of the hooks 105 of buckle 104 within the loops 122 during application of belt 100 as a tourniquet.

As shown in the Figures, embodiments of the tourniquet can include hooking means for hooking into or connecting with the anchoring means. According to one embodiment, the inventive tourniquet includes a buckle 104 having two hooks 105 that are each configured in size and shape to hook onto or otherwise attach to the anchoring means (e.g., the loops 122). One benefit of having two hooks 105 is a safety feature, and to enable use of the windlass tourniquet 100 even when one of the hooks 105 breaks. It will also be noted that is also possible to fasten both hooks 105 through the same or different anchors so as to provide an even more secure connection than would be possible with only a single hook 105.

The two hooks 105, extending/hooking from the buckle 104 in opposite directions also enables the same buckle 104 to be used in the windlass tourniquet 100 from different sides and/or with different hands (e.g., pulling/securing the buckle 104 with the right hand or the left hand).

Notwithstanding the benefits of a two hook configuration, it will also be appreciated that certain embodiments of the invention utilize only a single hook 105 or another hooking means that might be less expensive to manufacture or that might be lighter in weight than the two hook configuration.

According to one embodiment, the buckle 104 of the belt 100 includes additional structure, such as a military style belt anchor, for anchoring the belt to a helicopter or another vehicle.

As suggested above, tourniquet 100 can be used as a belt, a harness, rifle sling or another object incorporating belt type straps 102 and buckles 104. When worn as a belt, the tourniquet 100 will have a configuration similar to what is shown in FIGS. 1A-1B, with the buckle 104 being attached to only the main belt strap 102 passing through the buckle 104. Alternatively, when the belt is selectively used as a tourniquet, the belt will have a configuration similar to what is shown in FIGS. 6A-6B, with one or more of the buckle hooks 105 connected to one or more of the anchoring loops 122 on the inside of the belt 100.

Figure 6A:
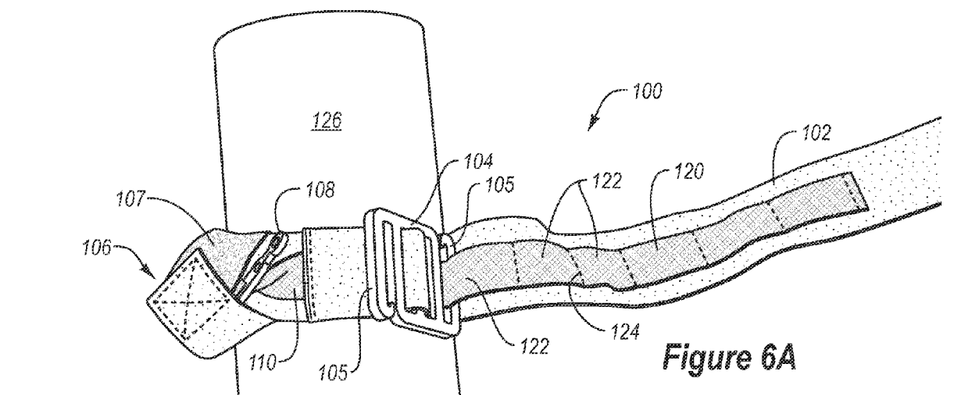
FIGS. 6A-6B show examples of the windlass tourniquet in an applied tourniquet position, with a hook from each belt/sling/harness passing through an anchoring loop.
Figure 6B:
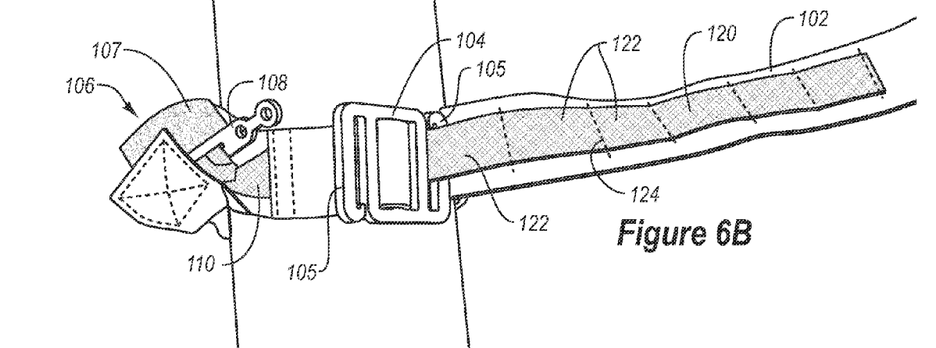

FIGS. 6A-6B illustrate differently colored examples of the windlass tourniquet 100 in an applied tourniquet position, with a hook 105 from each belt/sling/harness passing through an anchoring loop 122. As mentioned above, the plurality of anchors (e.g. loops 122) enables the belt/sling/harness 100 to be secured in a tourniquet ready position around a variety of differently sized objects (e.g., differently sized arms, legs, and so forth).

It will be appreciated that the configuration of the tourniquet components enables the tourniquet to be applied even in low visibility and no visibility environments and circumstances. In particular, the anchoring loops 122 and the buckle hooks 105 are configured in such a way that a user can feel the loops 122 and the hooks 105 and can connect the hooks 105 to the loops 122 without having to see the anchoring connection taking place. The dual hook configuration also enables at least one of the hooks 105 to be easily accessible and usable from different angles (to connect the hook 105) and even when the tourniquet 100 is applied with a single hand, and irrespective of which hand is used.

FIGS. 6A-6B also illustrate the windlass crank 108 in a rotated position, having been rotated in such a way as to tighten the windlass strap 110 (as described above). This tightening of the windlass strap 110 effectively tightens the main strap 102 (e.g. belt/harness/sling) around the object 126 the belt 100 is secured around. In this manner, the belt 100 operates as a tourniquet that is tightened to a desired tightness by the rotation of the windlass crank 108. The more the windlass crank 108 is rotated, the tighter the belt 100 cinches around the object 126. The rotated crank 108 is held is place by the securing means 106, such as the additional Nylon/Velcro 107 strapping material 106, so as to keep the windlass strap 110 and belt 100 in a tightened state and such that the tourniquet 100 will continue to apply the desired amount of pressure on the object 126.

In view of the foregoing, it will be appreciated that the present invention provides an inventive belt 100 having an integrated windlass tourniquet that can be fairly easily applied, secured and released, when appropriate, and even in low visibility conditions and even when use is limited to a single hand.

The present invention also applies to methods for applying a tourniquet with the foregoing described belts/slings/harnesses, by securing a buckle 104 of the belt/sling/harness (such as with a hook 105) to at least one loop 122 or other anchor disposed on the inside of the belt/sling/harness 100, while the belt/sling/harness is wrapped around an object 126 (such as a leg, an arm or another object). The windlass crank 108 is then rotated by hand or another tool until the belt 100 is tightened around the object 126 to a desired tightness. To minimize the amount of cranking or rotating of the windlass crank 108 that is necessary to provide the desired tightness, the belt/sling/harness 100 is preferably pulled tightly around the object 126 prior to connecting the hook 105 with the anchor (e.g. loop 122) and such that the anchor and hook 105 already hold the belt/sling/harness in a substantially tight position around the object 126. Once the belt/sling/harness is tightened to a desired tightness, by rotating the windlass crank 108, the windlass crank 108 is then secured in place by a securing means, such as the Velcro® strapping 106, 107.

In view of the foregoing, it will be appreciated that the present invention provides various belts, assemblies and methods incorporating windlass tourniquet components and pulley components. It will also be appreciated that the present invention may be embodied in other specific forms without departing from its spirit or essential characteristics. The described embodiments are therefore to be considered in all respects only as illustrative and not restrictive. Accordingly, it will be appreciated that the term "belt" is interchangeable with the term "strap", "sling" or "harness", inasmuch as the windlass tourniquet can also be incorporated into rifle slings, harnesses and other objects having belt or strap like features. Accordingly, while the Figures of the present invention specifically show belts, the present invention also applies to improved harnesses, straps, rifle slings, or any other objects having an integrated windlass tourniquet and which are configured to include any appropriate combination of the windlass tourniquet features described above.

The present invention also extends to methods for manufacturing integrated windlass tourniquets assemblies by attaching any appropriate combination of the windlass tourniquet components described above to a harness, a belt, a sling, a strap or another object, and which enables the object to operate as a both a harness, belt, sling, strap or other object, as well as a windlass tourniquet.

III. Windlass Tourniquets With Pulley Components

Windlass tourniquets having integrated pulley components are illustrated in FIGS. 7A- 11. These embodiments can also be modified to include any combination of the windlass tourniquet features described in reference to FIGS. 1A-6B.

In some embodiments, the windlass tourniquets are also configured with pulley means for facilitating the tightening of the windlass and corresponding tourniquet. In particular, the pulley means can provide a mechanical advantage during tightening of the tourniquet (and during operation of the windlass) and by reducing the amount of force that is required to rotate the windlass crank during the tightening of the tourniquet. The pulley means can also help minimize or reduce bunching and twisting of the main tourniquet strap during tightening by pulling excessive strap material over the main strap portion, as described herein.

Figure 7A:
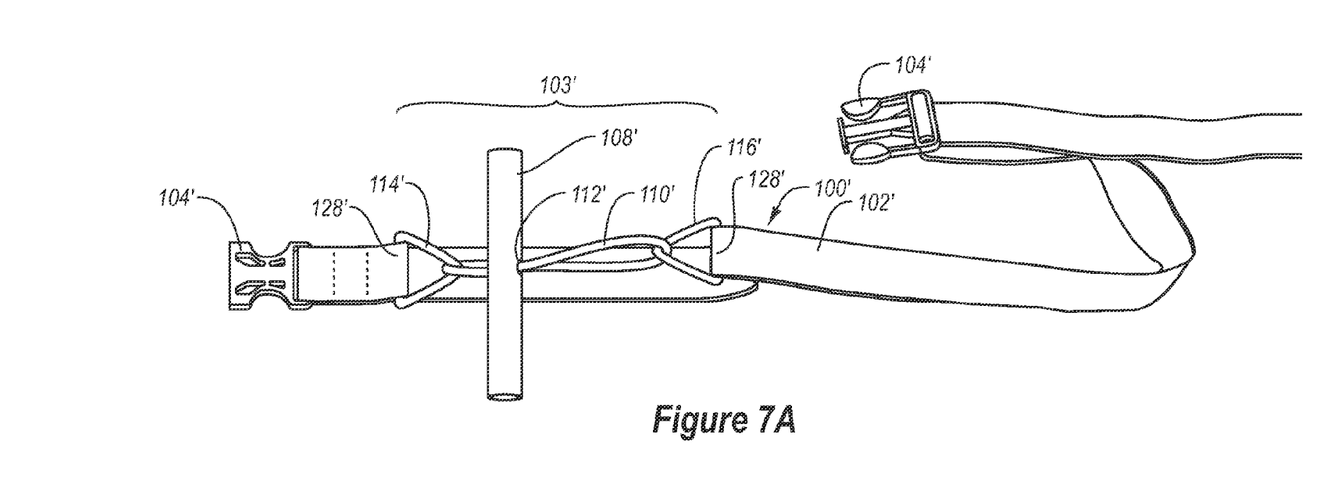
FIGS. 7A-7D show four windlass tourniquets that have been configured with various pulley components that comprise suitable non-limiting examples of the aforementioned pulley means for facilitating the tightening of the windlass tourniquet.
Figure 7B:
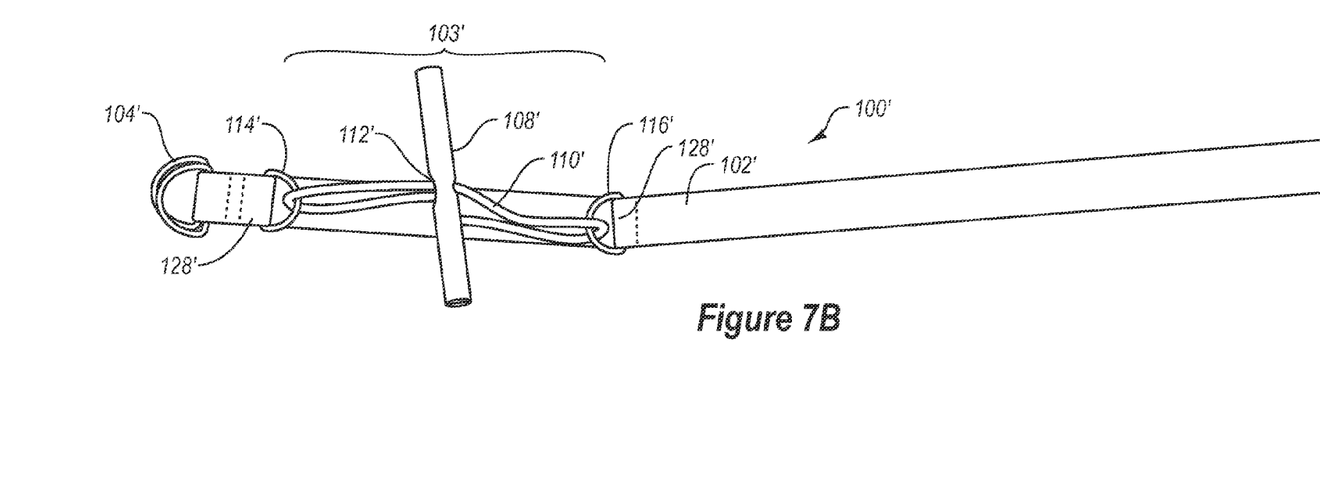
Figure 7C:
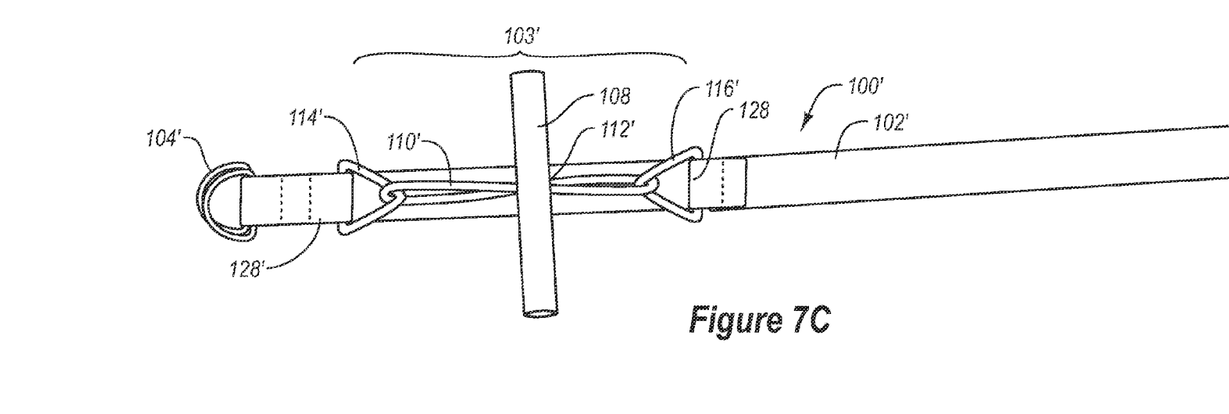
Figure 7D:
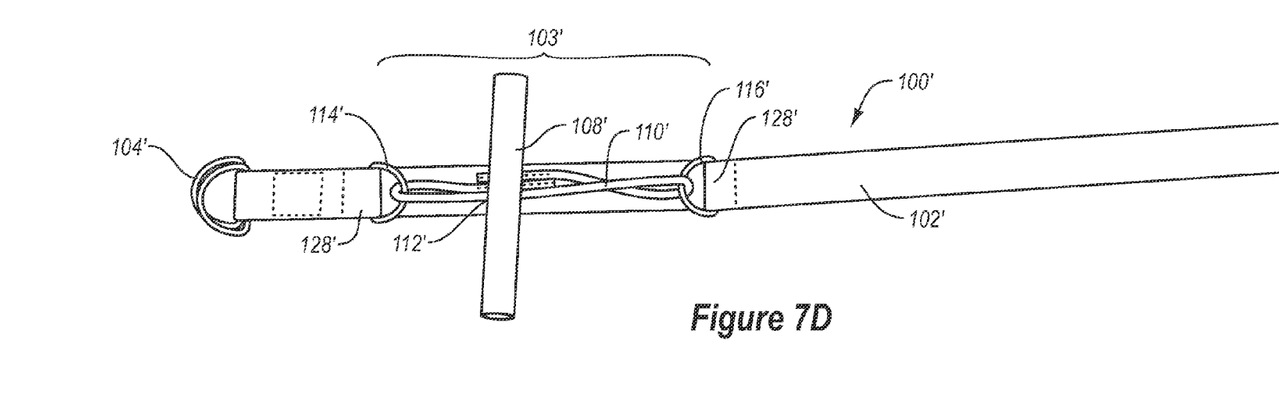

FIGS. 7A-7D illustrate four windlass tourniquets 100' that have been configured with various pulley components that comprise suitable non-limiting examples of the aforementioned pulley means for facilitating the tightening of the windlass tourniquet. The four tourniquet examples are referred to as Windlass Pulley Tourniquet Example 1 (FIG. 7A), Windlass Pulley Tourniquet Example 2 (FIG. 7B), Windlass Pulley Tourniquet Example 3 (FIG. 7C) and Windlass Pulley Tourniquet Example 4 (FIG. 7D).

Each of the Windlass Pulley Tourniquet Examples (1-4) includes a main tourniquet strap 102'. As labeled in FIGS. 7A-7D, the main tourniquet strap 102' also includes an active section 103'. It will be appreciated, however, that the naming of the active section does not imply that the remainder of the main tourniquet strap 102' is inactive. Instead, the naming of the active section is a mere convenience used for describing the overlapping functionality that occurs at the active section 103', as will be described below in more detail, and which generally includes the pulling or sliding of excessive strap material over the active section 103' during tightening of the tourniquet and so as to avoid or minimize bunching of the strap 102' within at least the active section 103'.

Each of the Windlass Pulley Tourniquet Examples (1-4) also includes an attachment means for securely enclosing the tourniquet about an object, such as an arm, a leg or other object. In some instances, the attachment means includes a buckle 104', such as a Fastex buckle, or another buckle, as shown by Windlass Pulley Tourniquet Example 1. In other instances, the attachment means includes double loop buckles 104', such as illustrated in Windlass Pulley Tourniquet Examples (2-4). These double buckles 104' are configured to receivably engage and securely hold the strap 102' in place when the strap 102' is fed through the buckles 104' in a standard manner that is well known to those of skill in the art of buckle fastening.

In addition to the buckles shown, it will be appreciated that other types of attachment means can also be used, including, but not limited to Velcro® hook and loop fasteners, snaps, hooks, loops and knots. It should also be appreciated that preferably, although not necessarily, the buckles, loops or other attachment means also double in functionality for attaching the strap/tourniquet to a gun, a bag, a harness or another object.

FIGS. 7A-7D also illustrates how each of the Windlass Pulley Tourniquet Examples (1-4) includes a windlass crank 108' and pulley cords 110' that can be fed through or otherwise attached to the windlass crank 108'. In the present embodiments, the windlass crank 108' includes a lightweight, yet strong pipe material, such as a PVC pipe material. However, it will be appreciated that the windlass crank 108' can also embody the configurations described above in reference to FIGS. 1A-6.

In yet other embodiments, the windlass crank is an independent and detachable component from the pulley cord 108' and is only attached at the time of use (during tightening of the tourniquet). In these embodiments, attachment means are provided for detachably attaching the windlass crank 108' to the pulley cord 110'. For example, the windlass crank 108' can include a slot 112' that is configured to receive and engage the pulley cord 110' and such that rotation of the crank 108' will apply a tension force on the pulley cord 110'.

In yet other embodiments, it is the pulley cord 110' that comprises the attachment means, rather than the windlass crank 108', for detachably attaching the windlass crank 108'. For example, the pulley cord 110' can include a loop formed by a knot or a fastener placed about the pulley cord 110', or a separate object attached to the pulley cord 110', in a localized region and that is configured in size and shape to receive the windlass crank 108'. In this embodiment, the windlass crank 108' can comprise a rod, a stick, or any other item that can be inserted through the loop and that can be rotated to twist the pulley cord 110' and to tighten the tourniquet. This embodiment can be particularly beneficial for minimizing the profile of the windlass components during periods of non-use (by detaching the windlass crank 108' during non-use, for example). The strap 102' of the tourniquet can also be configured to hold a specialized and detachable windlass crank 108' so that it does not create a protrusion from the tourniquet strap 102' (such as in a pocket formed in the strap 102') and until it is needed.

In some embodiments, the tourniquet 100' also includes windlass components, such as those described in the embodiments shown in FIGS. 1-6, which securely hold the windlass crank 108' in a fixed position during periods of use (after tightening the windlass crank 108'), as well as during periods of non-use. One way to do this is through the use of Velcro® hook and loop securing straps, for example, that are attached to the strap 102' and that are configured to enclose the windlass components.

Attention is now directed to the pulley anchors 114', 116', which are attached to the main strap 102' (as shown in each Example 1-4) near the ends of the active sections 103' of the main strap 102'. The pulley anchors 114', 116' are configured to freely receive the pulley cords 110' that are fed through the pulley anchors 114', 116'. In some embodiments, such as Examples 1 (FIG. 7A) and 3 (FIG. 7C), the pulley anchors 114', 116' are composed of angularly shaped loops. This can help orient the pulley cord(s) 110' during use in a predetermined configuration. In other embodiments, the pulley anchors 114', 116' are formed out of circular or semi-circular shaped loops, as shown in Examples 2 (FIG. 7B) and 4 (FIG. 7D). In yet other examples, not shown, the pulley anchors comprise grommets or other objects formed directly into the strap surface 102'.

Preferably, although not necessarily, the pulley anchors 114', 116' are attached to or formed within strap tabs 128' sewn into the main strap 102' at the ends of the active section 103' of the strap 102' and that protrude away from the strap 102'.

During use, as the windlass crank 108' is rotated and the pulley cord 110' attached to the windlass crank 108' is twisted, the pulley cord 110' is tightened and applies a pulling force to the pulley anchors 114', 116'. This pulls the pulley anchors 114', 116' towards each other, and towards the windlass crank 108', thereby tightening the tourniquet. Notably, the configuration of the pulley anchors 114', 116' and the pulley cord 110' enables a mechanical pulley advantage to be realized during tightening of the windlass. In particular, the mechanical pulley advantage reduces the force required to pull the pulley anchors 114', 116' towards one another. However, the mechanical advantage realized by use of this pulley configuration can vary, depending on the friction applied between the pulley cord 110' and the pulley anchors 114', 116' and the number of pulley anchors used. To maximize the mechanical pulley advantage, it is desirable, although not necessary, to manufacture the pulley anchors 114', 116' and pulley cords 110' out of materials that have low frictional coefficients.

In some embodiments, the pulley cord 110' is a nylon cord and the pulley anchors 114', 116' are manufactured out of a metal. The pulley anchors 114', 116' can also be manufactured out of a strong plastic, including, but not limited to plastics having a Teflon® or other slip coating. Other materials can also be used. For example, the pulley cord 110' can also be manufactured out of an elastic material, such as a bungee type material, to add additional flexibility and different degrees of tightness when applied.

As mentioned above, the mechanical advantage provided by the pulley means can also vary, depending on the number of pulley anchors 114', 116' that are used. For example, in one embodiment, only a single pulley anchor is used and the pulley cord 110' is simply fastened to an alternate end of the active section 103' of the strap 102' from the end where the pulley anchor is attached. This embodiment can reduce the manufacturing costs while still providing about one half of the mechanical advantage that is provided by the two pulley anchor embodiments shown in FIGS. 7A-7D.

Another advantage provided by the current embodiments (incorporating the pulley components described above) is the reduction in the bunching of the strap 102' that could otherwise occur during tightening of the tourniquet. In particular, it will be noted that while the pulley anchors 114', 116' are pulled inwardly, towards the center of the active section 103' of the tourniquet strap 102', that the tabs 128' attached to the pulley anchors 114', 116' are pulled up and over the active section 103' of the strap 102', along with the other strap material that is made available during the tightening process. This effectively reduces or prevents bunching of the strap material 102' within at least the active section 103' of the strap 102' and in some instances the entire strap 102'.

Reducing bunching (and twisting) of the strap 102' during tightening of the tourniquet is an advantage over prior art tourniquets. Initially, this reduced bunching can provide a more comfortable application of the tourniquet. This can also result in a more uniform and clean application of the tourniquet strap around the treatment area. This is particularly advantageous for reducing potential damage to sensitive nerves and other tissues that can become pinched or otherwise damaged during application of tourniquet that results in twisting or bunching of the tourniquet strap.

Before moving on to the other FIGS. (8-11), attention will be directed to the difference between the Windlass Pulley Tourniquet Example 2 (FIG. 7B) and the Windlass Pulley Tourniquet Example 4 (FIG. 7D), which have very similar appearances. One difference between these Examples (2 & 4) is the configuration of the pulley cord 110'. In particular, it is noted that the pulley cord 110' in the Windlass Pulley Tourniquet Example 2 (FIG. 7B) is formed into a continuous floating loop that is not attached directly to the main strap 102', but that only passes through the pulley anchors 114', 116' and windlass crank 108' a single time. The ends of the pulley cord 110' are then tied together (shown below the windlass crank 108'), glued together, or attached together with mechanical fasteners attached to the ends of the pulley cord ends, such as threaded, hooked or other type fasteners.

The pulley cord of the Windlass Pulley Tourniquet Example 4 (FIG. 7D) is a little different than the pulley cord presented by the Windlass Pulley Tourniquet Example 2 (FIG. 7B). In particular, while the pulley cord 110' in Example 4 (FIG. 7D) is passed through the pulley anchors 114', 116' and windlass crank 108' a single time, as in Example 2 (FIG. 7B), the ends of the pulley cord 110' are physically attached to the main tourniquet strap 102', rather than being freely attached to each other. As shown, for example, the ends of the pulley cord 110' are sewn directly to the active section 103' of the strap 102'. One advantage of this embodiment is the elimination of the potential for the knot or other fastener, which is used to connect the ends of the pulley cord 110' together, to become entangled with one of the pulley anchors 114', 116'. (It will be appreciated that if the pulley cord 110' were to become entangled with the pulley anchor, it could reduce the mechanical benefit provided by the pulley anchor and that is only provided when the cord 110' is enabled to freely pass through the pulley anchor during tightening).

Lastly, with regard to FIGS. 7A-7D, it is noted that all of the tourniquets 100' are shown to have a strap 102' of substantially the same width. This, however, is not a requirement. While it is generally advisable to provide a tourniquet width of at least one inch, to reduce the risk of cutting into or damaging tissue surrounding the treatment area, the width of the tourniquets of the present invention can vary in size to accommodate any need or preference. For example, it will be noted that the tourniquets of the present invention can be incorporated into existing slings, such as slings for bags, guns, harnesses, or other objects. Accordingly, the width of the strap 102' can vary to utilize the natural width of the straps and slings used in those existing objects and configurations.

According to some embodiments, the width of the strap 102' is about one inch. In other embodiments, the width of the strap 102' is less than one inch. In yet other embodiments, the width of the strap 102' is between about one inch and two inches. In some embodiments, the width of the strap 102' is two or more inches.

It will also be appreciated that while the strap 102' is shown to be manufactured out of a standard Nylon strap, that the material used to manufacture the strap 102' can vary to accommodate different needs and preferences, including inelastic materials, as well as elastic materials. The thickness of the strap 102' can also vary.

Figure 8:
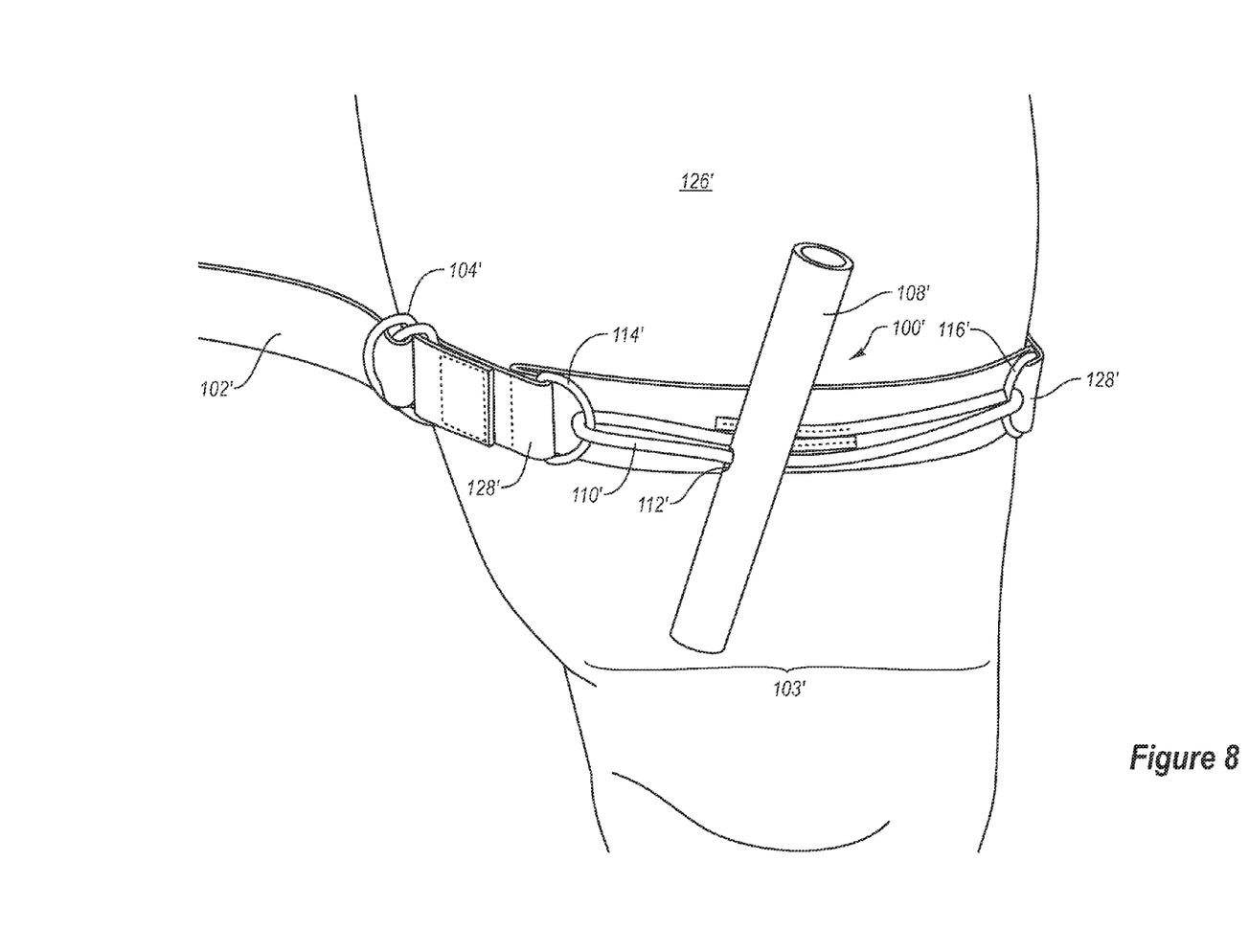
FIG. 8 shows the windlass pulley tourniquet of FIG. 7D in an attached position around a person's leg, in a pre-tightened state.
Figure 9:
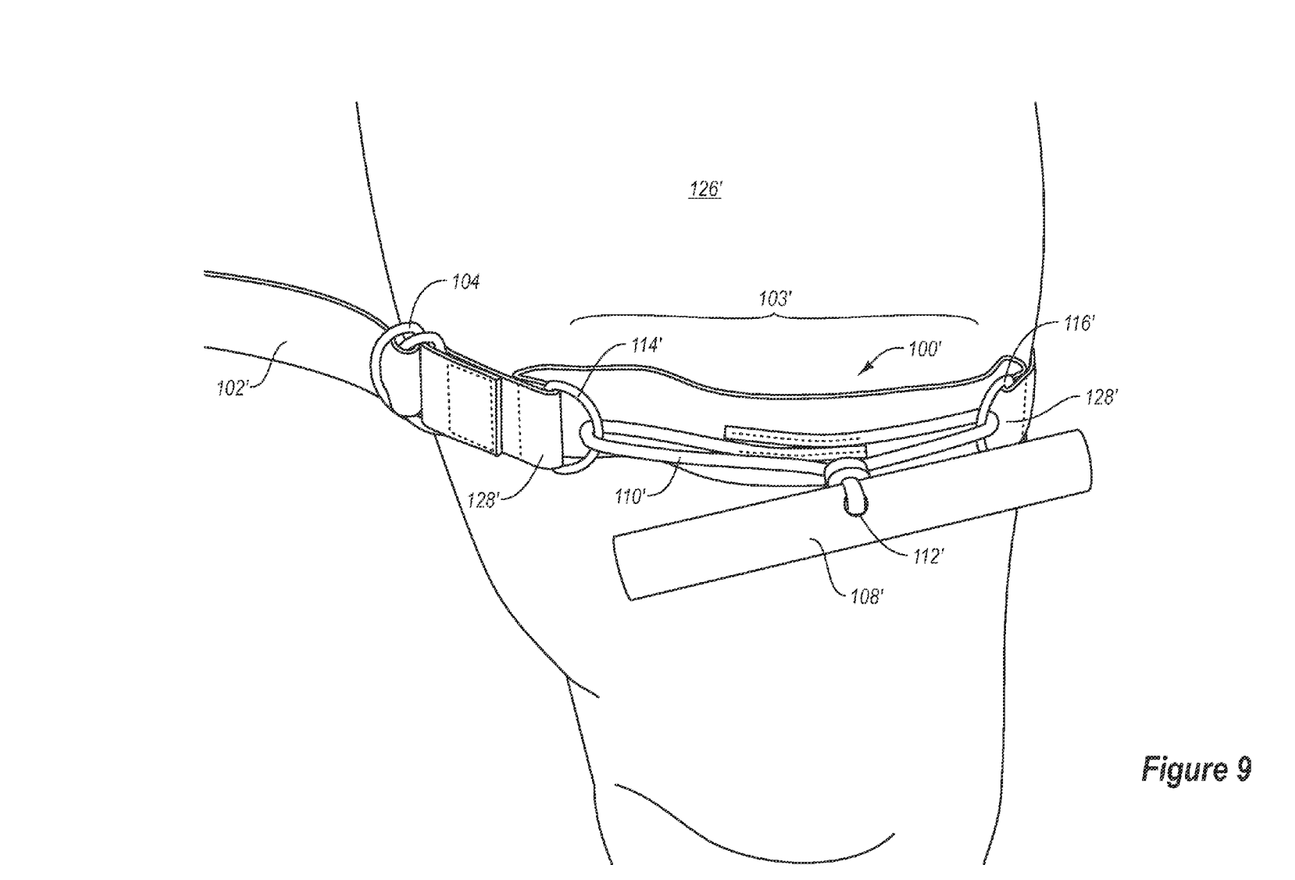
FIG. 9 shows the tourniquet and leg of FIG. 8 with the tourniquet in a tightened state.

Attention is now directed to FIGS. 8-11, which illustrate applications of the Windlass Pulley Tourniquets in various states. As shown in FIG. 8, for example, the Windlass Pulley Tourniquet 100' of Example 4 (FIG. 7D) is shown in an attached position around a person's leg 126', in a pre-tightened state. FIG. 9 illustrates the same tourniquet 100' (Windlass Pulley Tourniquet Example 4—FIG. 7D) in a tightened state, which is accomplished by rotating the windlass crank 108' until the pulley cord 108' is twisted and the pulley anchors 114', 116' are pulled inwardly.

Figure 10:
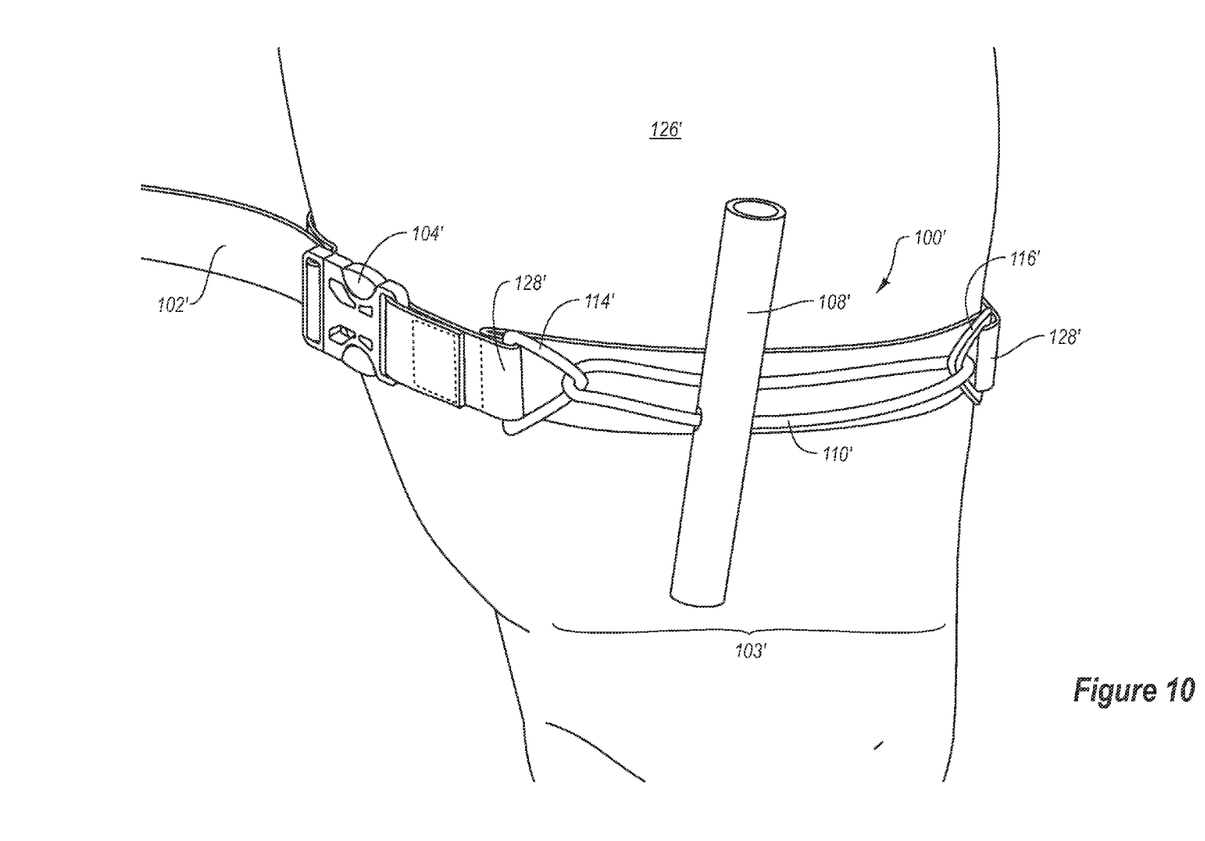
FIG. 10 show the windlass pulley tourniquet of FIG. 7A in an attached and pre-tightened state around a leg.
Figure 11:
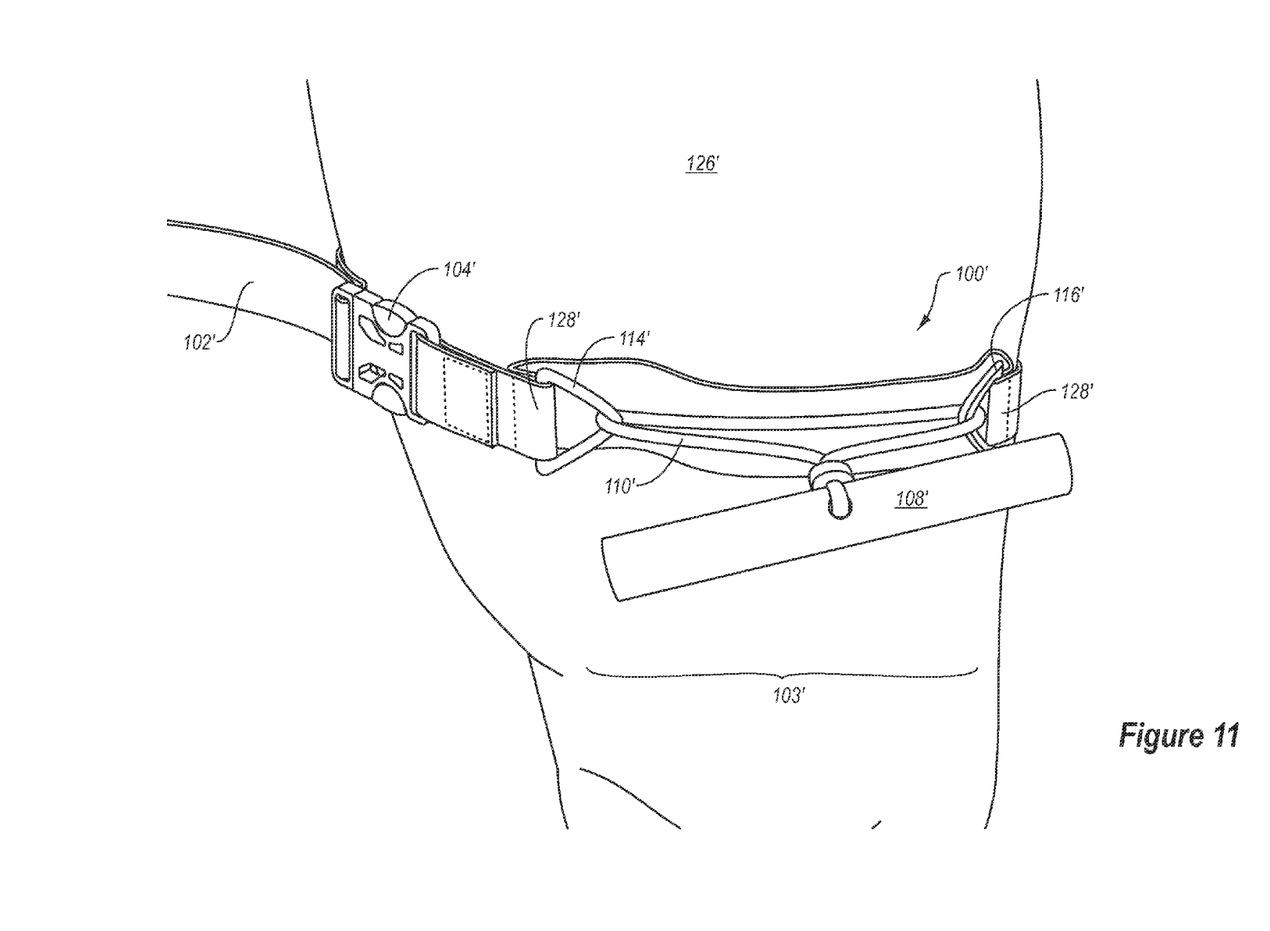
FIG. 11 shows the tourniquet and leg of FIG. 10 in a tightened state after rotating the windlass crank.

FIGS. 10 and 11 similarly show the Windlass Pulley Tourniquet 114', 100' Example 1 of FIG. 7A in an attached and pre-tightened state around a leg 126' (FIG. 10), as well as in a tightened state (FIG. 11), after rotating the windlass crank 108'.

Once the tourniquet is tightened, the windlass crank 100' is secured into a fixed position. This can occur, as described above with reference to FIGS. 1-6, with the use of a windlass strap or similar securing means.

In some embodiments, the windlass crank 108' is manufactured in size and shape to include securing means that will securely engage with the pulley anchors 114', 116' and in such a way to secure the windlass crank 108' in a fixed position. For example, in one instance, the windlass crank 108' is configured with such a length and diameter that at least one arm of the windlass crank 108' can be positioned into and through at least one of the pulley anchors 114', 116' after tightening the tourniquet.

In another embodiment, the windlass crank 108' is configured with one or more hooks that are configured in size and shape to engage the structure of the pulley anchor and to prevent the windlass crank 108' from unwinding.

In summary, it will be appreciated that the foregoing embodiments of windlass tourniquets, including the windlass tourniquets having pulley components, can provide advantages over existing tourniquets, not only due to the mechanical advantages provided through the windlass and pulley components, but also in their adaptability for use in existing straps, slings, belts, harnesses and other objects.

Despite the specific examples provided above, it will also be appreciated that the scope of the invention also extends to tourniquets incorporating any combination of the features described herein and that are manufactured out of different types of materials that are suitable to provide the functionality described above.

What is claimed is:

1. A windlass tourniquet assembly, comprising:
   an elongate main strap extending between a first end and an opposite second end;
   attachment means for attaching the first end of the main strap to the second end of the main strap, at least a portion of the attachment means being disposed at the first end of the elongate main strap;
   a first pulley anchor fixedly attached to the main strap at a first location between the first and second ends;
   a second pulley anchor fixedly attached to the main strap at a second location between the first and second ends;
   a windlass pulley cord freely passing through the first pulley anchor and the second pulley anchor, such that the windlass pulley cord is slidably engaged with both of the first pulley anchor and the second pulley anchor,
   a length of an active section of the main strap being defined between the first location and the second location where the first pulley anchor and the second pulley anchor are attached, respectively, to the main strap; and
   an elongate windlass crank that is attachable to the windlass cord during use, wherein the windlass cord is twisted when the windlass crank is rotated during use, with the windlass cord sliding in engagement with at least one of the first pulley anchor and the second pulley anchor, thereby pulling the first pulley anchor and the second pulley anchor in an inward direction towards the windlass crank, effectively shortening the length of the active section of the main strap and thereby tightening the main strap during said use.

2. A tourniquet assembly as recited in claim 1, further comprising securing means for securing the windlass crank, the securing means extending in a perpendicular direction relative to the main strap, the securing means being disposed at the first end of the main strap.

3. A tourniquet assembly as recited in claim 2, wherein the securing means comprises hook and loop securing straps, the securing straps being configured to be securely positioned around the windlass crank so as to hold the windlass crank in a substantially secure position after rotation of the windlass crank during use.

4. A tourniquet assembly as recited in claim 1, wherein the windlass crank includes a hole disposed through a center portion of the windlass crank through which the windlass strap is disposed.

5. A tourniquet assembly as recited in claim 1, wherein the windlass crank is formed of at least one of steel, aluminum, or PVC.

6. A tourniquet assembly as recited in claim 1, wherein ends of the windlass crank are textured to facilitate gripping and rotation of the crank by hand.

7. A tourniquet assembly as recited in claim 1, further comprising a sleeve disposed on the main strap within which at least a portion of the windlass strap is hidden and protected.

8. A tourniquet assembly as recited in claim 1, wherein the attachment means comprises a double pass buckle.

9. A tourniquet assembly as recited in claim 1, wherein the main strap has a length between 30 and about 50 inches.

10. A tourniquet assembly as recited in claim 1, wherein the main strap has a width between 1 inch and about 3 inches.

11. A tourniquet assembly as recited in claim 1, wherein the pulley anchors comprise a low friction slip material to reduce sliding friction of the windlass pulley cord against the pulley anchors.

12. A tourniquet assembly as recited in claim 1, wherein the pulley cord comprises an elastic material.

13. A windlass tourniquet assembly, comprising:
an elongate main strap extending between a first end and an opposite second end;
a buckle at the first end of the elongate main strap;
a first pulley anchor forming a first loop that is fixedly attached to the main strap proximate the first end;
a second pulley anchor forming a second loop fixedly attached to the main strap between the first end and the second end;
a windlass cord forming a third loop that is slidably interconnecting the first pulley anchor and the second pulley anchor, such that the windlass cord freely passes through the first loop in the first pulley anchor as well as through the second loop in the second pulley anchor; and
an elongate windlass crank that is attached to the windlass cord in such a manner as to cause the windlass cord to be twisted when the windlass crank is rotated, thereby causing a portion of the windlass cord to slide against at least one of the first pulley anchor or the second pulley anchor, effectively shortening a length of the windlass cord by pulling the first pulley anchor and the second pulley anchor closer together, and thereby tightening the main strap for use as a tourniquet.

14. A windlass tourniquet assembly, comprising:
an elongate main strap extending between a first end and an opposite second end;
attachment means for attaching the first end of the main strap to the second end of the main strap, at least a portion of the attachment means being disposed at the first end of the elongate main strap;
a first pulley anchor fixedly attached to the main strap near the attachment means;
a second pulley anchor fixedly attached to the main strap a predetermined distance away from the attachment means;
a windlass pulley cord slidably engaged with the first pulley anchor and slidably engaged with the second pulley anchor and defining a length of the pulley cord between the first pulley anchor and the second pulley anchor, wherein the windlass pulley cord passes through each of the first pulley anchor and the second pulley anchor only a single time, while forming a closed loop; and
an elongate windlass crank that is attached to the windlass pulley cord in such a manner that the windlass pulley cord is twisted when the windlass crank is rotated, effectively shortening the length of the windlass pulley cord and thereby tightening the main strap for use as a tourniquet.

15. A windlass tourniquet assembly as recited in claim 14, further comprising an anchor strap for anchoring the attachment means in a position for applying the windlass tourniquet assembly, the anchor strap being disposed on a back surface of the main strap opposite from a front surface of the main strap and being attached to the main strap at a plurality of different positions to form a plurality of loops between the anchor strap and the main strap.

16. The windlass tourniquet assembly of claim 14, wherein a first end of the windlass pulley cord and a second end of the windlass pulley cord connect directly to the main strap, such that the windlass pulley cord and the main strap collectively form a closed loop.

17. The windlass tourniquet assembly of claim 14, wherein a first end of the windlass pulley cord and a second end of the windlass pulley cord are connected together, thereby forming the closed loop.

18. The windlass tourniquet assembly of claim 17, wherein the closed loop is a floating loop inasmuch as the closed loop is only connected to the main strap by way of the pulley anchors, without being directly connected to the main strap.

19. The windlass tourniquet assembly of claim 18, wherein an outer portion of the closed loop is disposed on an outer side of the pulley anchors, the outer portion extending between the first and second pulley anchors, and wherein an inner portion of the closed loop is disposed on an inner side of the pulley anchors, with the outer portion of the closed loop being attached to the windlass crank by passing through an opening in the windlass crank and while the entire inner portion of the closed loop remains outside of the opening in the windlass crank.

20. The windlass tourniquet assembly of claim 14, wherein the windlass pulley cord passes through an opening in the windlass crank only a single time.

21. The windlass tourniquet assembly of claim 14, wherein at least one of the first pulley anchor or the second pulley anchor is visibly exposed on the main strap.

22. The windlass tourniquet assembly of claim 14, wherein both of the first pulley anchor and the second pulley anchor are visibly exposed on the main strap.

23. The windlass tourniquet assembly of claim 14, wherein the windlass tourniquet assembly further includes at least one securing strap for selectively securing the windlass crank in a fixed position.

* * * * *